United States Patent [19]

Küppenbender et al.

[11] Patent Number: 5,061,349
[45] Date of Patent: Oct. 29, 1991

[54] METHOD OF ISOLATING TRIOXANE FROM AQUEOUS TRIOXANE SOLUTIONS BY DISTILLATIVE SEPARATION

[76] Inventors: Herbert Küppenbender, Lenzhahner Weg 36, 6272 Niedernhausen; Helmut Reis, Koehlerweg 15, 8751 Hofstetten, both of Fed. Rep. of Germany

[21] Appl. No.: 558,804

[22] Filed: Jul. 27, 1990

Related U.S. Application Data

[63] Continuation-in-part of Ser. No. 287,642, Dec. 20, 1988, abandoned, which is a continuation-in-part of Ser. No. 141,069, Jan. 5, 1988, abandoned.

[51] Int. Cl.$^5$ ................... B01D 3/34; C07D 323/06
[52] U.S. Cl. ........................... 203/14; 203/49; 203/82; 203/84; 203/87; 549/368
[58] Field of Search ............. 203/14, 49, 82, 84, 203/87; 159/47.1, 901, DIG. 23; 202/161, 186, 201; 549/368

[56] References Cited

U.S. PATENT DOCUMENTS

| | | | |
|---|---|---|---|
| 2,257,780 | 10/1941 | Bludworth | 203/87 |
| 2,347,447 | 4/1944 | Walker | 203/96 |
| 2,675,346 | 4/1954 | McLean | 203/87 |
| 3,197,437 | 7/1965 | Wall | 549/368 |
| 3,313,713 | 4/1967 | Martin | 549/368 |
| 3,378,468 | 4/1968 | Langecker | 549/368 |
| 3,401,096 | 9/1968 | Wondrak | 203/87 |
| 3,426,040 | 2/1969 | Langecker | 549/368 |
| 3,493,472 | 2/1970 | Schumacher | 202/183 |
| 3,697,546 | 10/1972 | Asakawa et al. | 549/368 |
| 4,043,873 | 8/1977 | Ackermann et al. | 549/368 |
| 4,340,542 | 7/1982 | Bär et al. | 549/368 |
| 4,348,540 | 9/1982 | Ferris et al. | 203/87 |
| 4,493,752 | 1/1985 | Naito et al. | 549/368 |
| 4,563,536 | 1/1986 | Yoshida et al. | 549/368 |

FOREIGN PATENT DOCUMENTS

| | | | |
|---|---|---|---|
| 0771679 | 11/1967 | Canada | 549/368 |
| 0160977 | 7/1984 | Fed. Rep. of Germany | 549/368 |
| 3310116 | 8/1984 | Fed. Rep. of Germany | 202/183 |
| 49-28197 | 7/1974 | Japan | 549/368 |
| 59-186975 | 10/1984 | Japan | |

Primary Examiner—Virginia Manoharan
Attorney, Agent, or Firm—Michael J. Striker

[57] ABSTRACT

A method of isolating trioxane by distillative separation at atmospheric pressure without extraction steps from an aqueous trioxane solution having a trioxane concentration which does not exceed that concentration, which has an constant boiling azeotropic mixture obtained at a simple distillation of said aqueous trioxane solution at normal pressure, includes heating the aqueous trioxane solution, which may also contain formaldehyde and acid, in an evaporator to form a trioxane and water vapor-containing steam mixture substantially of the azeotrope boiling temperature (about 92° C. for a solution containing only water and trioxane); feeding an inert gas stream into either the evaporator or a partial condenser connected directly to the evaporator; leading the steam mixture in a first stage together with the inert gas stream through the partial condensing means, wherein the steam mixture together with the inert gas stream is cooled to a temperature of 58° to 64° C. and a water portion of the steam mixture is partially condensed together with the formaldehyde, if present, and separated; then in a second stage leading the steam mixture together with the inert gas stream through a condenser, wherein the trioxane portion is condensed together with the remaining water portion and separated from the inert gas stream to form a trioxane concentrate having a trioxane concentration which is greater than that of the azeotropic mixture. Pure trioxane can then be obtained by simply distilling.

19 Claims, 3 Drawing Sheets

METHOD OF ISOLATING TRIOXANE FROM AQUEOUS TRIOXANE SOLUTIONS BY DISTILLATIVE SEPARATION

This application is a continuation-in-part of application Ser. No. 287,642 filed Dec. 20, 1988, now abandoned, which in turn is a continuation-in-part of application Ser. No. 141,069 filed Jan. 5, 1988, and abandoned June 20, 1988.

BACKGROUND OF INVENTION

The present invention relates to a method of isolating trioxane from an aqueous trioxane solution, which may contain formaldehyde, as further constituent by distillative separation techniques.

Trioxane has become more and more important, for example, as an intermediate product for the production of polyacetals. Trioxane is obtained by trimerizing formaldehyde, generally from an aqeuous formalin solution with a formaldehyde content of from about 30 to 70% by weight, which is heated up to boiling in a trioxane reactor in the presence of an acid catalyst. The so-formed trioxane is distilled off from the trioxane reactor in the form of a steam mixture substantially consisting of trioxane, water and formaldehyde. This steam mixture is the so-called synthesis steam. The acid catalyst remains in the reactor. The synthesis steam which includes about 12 to 16% by weight trioxane is normally fed into a rectifying column or tower connected to the trioxane reactor, whereby water and formaldehyde are concentrated in the tower sump, while a mixture with increased concentration in trioxane is obtained at the head of the tower. The trioxane-water-formaldehyde ratio in that mixture is about 35:48:17.

Pure trioxane cannot be isolated from mixtures with water or with water and formaldehyde by a simple distillation process at substantially atmospheric pressure, because trioxane forms azeotropic mixtures with water in the ratio of 70% by weight trioxane: 30% by weight water and with formaldehyde and water in the ratio of 65 to 60% by weight trioxane: 29 to 24% by weight water: 6 to 16% by weight formaldehyde.

To overcome the barrier to further trioxane purification due to formation of the azeotropic mixtures in the trioxane distillation, the trioxane containing mixture obtained in the head of the tower or rectifying column is normally subjected to an extraction treatment with an inert agent nonmiscible with water, for example, the hydrocarbon chlorides, methylene chloride or ethylene chloride, or benzene.

The disadvantage of the extraction treatment resides not only in that the separation of the trioxane from the extraction agent and its purification before reuse require additional operations, but also in that at working with organic solvents it cannot be avoided that the solvent would flow into the waste water and escape into the atmosphere, and such organic solvents, particularly hydrocarbon chlorides, especially when exposed to UV radiation, provide a strong environmental hazard.

It would thus be desirable to provide a method of isolating trioxane from an aqueous solution of trioxane, which may contain formaldehyde by a simple distillative method without an extraction step, at atmospheric or normal conditions of pressure.

SUMMARY OF INVENTION

It is an object of the present invention to provide an improved method of isolating trioxane from an aqueous trioxane solution without on extraction step at substantially atmospheric pressure.

It is also an object of the present invention to provide a method of isolating trioxane from an aqueous trioxane solution containing formaldehyde and being formed during the trioxane synthesis by a simple distillative method without an extraction step at substantially atmospheric or normal pressure conditions.

It is another object of the present invention to provide a method of isolating trioxane from an aqueous trioxane solution having a trioxane concentration less than that of the corresponding azeotropic mixture by a distillative separation, without extraction steps, at atmospheric or normal pressure conditions.

According to our invention the method of isolating trioxane by distillative separation at atmospheric pressure without extraction steps from an aqueous trioxane solution having a trioxane concentration which does not exceed that concentration which has a constant boiling azeotropic mixture obtained at a simple distillation of said aqueous trioxane solution at normal pressure, includes the steps of heating the aqueous trioxane solution, which may also contain formaldehyde and acid, in an evaporator to form a trioxane and water vapor-containing steam mixture substantially of the azeotrope boiling temperature; feeding an inert gas stream into either the evaporator or a partial condensing means connected directly to the evaporator; leading said steam mixture in a first stage together with the inert gas stream through the partial condensing means, wherein the steam mixture together with the inert gas stream is cooled to a temperature of 58° to 64° C. and a water portion of the steam mixture is partially condensed together with the formaldehyde, if present, and separated; then in a second stage leading said steam mixture together with said inert gas stream through a condenser, wherein said trioxane portion is condensed together with the remaining water portion and separated from said inert gas stream to form a trioxane concentrate having a trioxane concentration which is greater than that of the azeotropic mixture. Pure trioxane can then be obtained by simply distilling.

Advantageously the temperature range is between 60° and 62° C. during the partial condensation. The inert gas may be supplied to the lower portion of the evaporator. The second stage condensing step is advantageously performed at a temperature of from 30° to 50° C.

The inert gas may be selected from the group consisting of carbon dioxide, nitrogen, noble gas, air and air poor in oxygen with an oxygen content of about 10 to 12% by volume.

The partial condensing means of the first stage may be a partial condenser or a distillation column.

The aqueous trioxane solution from which the trioxane is to be isolated may be a water and trioxane containing mixture with a trioxane content up to about 70% by weight and a boiling point of about 92° C. or a water, formaldehyde and trioxane containing mixture which may contain said three components in a ratio up to 65 to 60% by weight trioxane, 29 to 24% by weight water and 6 to 16% by weight formaldehyde. The aqueous trioxane solution containing trioxane, water and formaldehyde in a ratio of about 35:48:17 and having a boiling point of from 96° to 98° C. which is produced by trioxane synthesis and known distillative separation can be used as the starting solution, too. The aqueous trioxane solution can also contain an acid.

The method may be operated continuously or discontinuously.

DETAILED DESCRIPTION OF THE INVENTION

It has been found that, during the separation of trioxane from an aqueous trioxane solution having a trioxane content less than or equal to that of the corresponding azeotropic mixture or solution the known solvent extraction steps and the disadvantages connected therewith can be avoided in a surprising simple manner in a process operating substantially at atmospheric pressure, if, upon heating up the aqueous trioxane solution to boiling in an evaporator, the steam mixture discharged therefrom, which has a temperature of about 92° C. is led in a first stage through a partial condensing means connected directly to the evaporator together with an inert gas stream which is supplied either into the evaporator or the lower portion of said partial condensing means. During the passage through said partial condensing means the steam-inert gas mixture is cooled down to a temperature of from 58° to 64° C., preferably 60° to 62° C., and thereby subjected to a fractional condensation at atmospheric pressure, whereby the water portion of the steam mixture is partially condensed and separated and the trioxane-containing portion of said mixture together with the inert gas stream are fed in a second stage into a condenser arranged directly after the partial condensing means. In the second stage condenser the trioxane and the residual water portion are condensed and separated from the inert gas stream.

In the partial condensing means of the first stage the water portion of the steam mixture is partially condensed and separated from the mixture. Since the so-produced condensate practically contains no more trioxane, it is possible with the partial condensation in the presence of the inert gas stream according to the present invention to selectively remove the entire water portion from the trioxane-containing steam mixture. For practical purposes the water portion is taken off only up to about 10% by weight.

Thus the trioxane portion of the mixture practically freed from water is delivered together with the inert gas stream to the condenser in the second stage of the process. A trioxane concentrate is produced by condensation in the condenser and separated from the inert gas stream.

The aqueous trioxane condensate obtained in the condensation in the second stage of the process can have at least 90% by weight trioxane advantageously and can be further processed to produce pure trioxane without any difficulty, for example by crystallization or by a simple distillation since the azeotrope barrier has been overcome by the process.

If the end product of the process of the invention is a concentrate having a trioxane concentration greater than that of the corresponding azeotropic mixture, the obtained concentrate can be further purified and freed of the residual water only by a single simple distillation.

The inert gas is conveniently supplied in a cyclic circulation to avoid trioxane losses. The inert gas can be fed into the evaporator or the lower part of the partial condensing means. The inert gas stream is preferably supplied into the bottom part of the evaporator, in order to obtain a good distribution in the solution contained in the evaporator. For this purpose the evaporator can be provided with distribution means including filling elements and distributor elements, for example, screens, nozzles, valves and bubble trays, which intensify the intermixing produced in the evaporator solution upon the supply thereinto of the inert gas stream.

If the distillative separation process of the present invention is performed discontinuously, the water portion of the mixture separated by the partial condensation in the first stage is fed back into the evaporator to maintain the required liquid volume. If the new liquid is continuously supplied to the evaporator as is the case in a continuous process, the water portion separated by the partial condensation is removed from the system.

The distillative method according to the present invention which produces a trioxane concentrate having more trioxane than the corresponding azeotrope can also be applied to trioxane solutions which contain formaldehyde in addition to water. Such solutions are produced in the synthesis of trioxane by trimerization of formaldehyde. The formaldehyde of the steam mixture which passes together with the inert gas stream through the partial condensing means, is cooled to a temperature in the range of 58° to 64° C., preferably 60° to 62° C., condensed together with the water portion of the steam mixture and separated. The trioxane portion containing only a small amount of residual water, which is subjected to the condensation in the presence of the inert gas stream in the second stage, practically has no formaldehyde.

Aqueous trioxane solutions containing trioxane, water and formaldehyde in the ratio of 35:48:17 which are obtained at the head of the rectifying column used in conventional synthesis methods to increase the trioxane content of the conventional synthesis steam can also be used as the starting solution in the method of the present invention. The trioxane which up to now could be isolated from such solutions only by the known solvent extraction now can be isolated by the distillative separation techniques of our invention.

The distillative trioxane separation process of our invention can also be applied to an acid, water and formaldehyde containing trioxane solution which is obtained by heating an acid, about 30 to 70% by weight, preferably 50 to 65% by weight, formaldehyde containing solution with a pH value which corresponds to that of the 0.5 to 25% by weight sulfuric acid. The trioxane is formed in situ in these solutions upon heating and distilled off from the raction vessel together with water and formaldehyde in the form of a steam mixture, the so-called synthesis steam, that contains no acid.

With the application of the distillative separation process according to the present invention to this solution the inert gas stream is fed into the evaporator, preferably into its bottom part, and together with this inert gas stream the distilled steam mixture is removed from the evaporator. This steam mixture which has a trioxane concentration of about 55% by weight and a temperature of about 92° C. is passed through the partial condensing means in a first stage. Here, the formaldehyde and the water portions of said steam-inert gas-mixture, upon being cooled to a temperature of from 58° to 64° C., preferably 60° to 62° C., are condensed and separated from the remaining mixture and/or fed back to the reactor to maintain the required liquid amount, depending on whether the process is continuous or discontinuous.

The trioxane portion of said steam mixture which together with the residual water portion and the inert gas stream is subjected to a condensation in the second stage is practically free of formaldehyde and the so obtained trioxane concentrate has a trioxane content of more than 90% by weight. It can be easily processed into water-free pure trioxane without use of solvent extraction steps, e.g. by a simple distillation.

When the distillative separation method of this invention is applied to an acid trioxane-containing formalin solution which forms, upon heating, further trioxane in situ, the inert gas stream can, together with gaseous formaldehyde, be fed into the evaporator. The gaseous formaldehyde does not affect the course of the separation process, because in the hot acid evaporator liquid it is immediately converted into trioxane which is distilled off from the evaporator in the form of the synthesis steam. The obtained synthesis steam-inert gas mixture is passed through the first and second stages of the process. The use of the inert gas containing formaldehyde makes it possible in a particularly simple fashion to continuously produce with the method of this invention trioxane concentrates with more than 90% by weight trioxane.

The formaldehyde-containing inert gas stream can be, for example, the formaldehyde gas coming from the catalytic methanol oxidation, for example from a Formox-process or silver contact process. In this case the inert gas portion of said formaldehyde-containing stream makes the separate supply of another inert gas stream for the process unnecessary.

The ratio between the inert gas and the steam in the steam-inert gas mixture is not critical. It is defined either by the trioxane production method or by reaching the gas saturation limit, the dew point which is pressure and temperature dependent. Starting with an aqueous trioxane solution which is evaporated during the process leads to a steam mixture which is supplied with only so much energy that the dew point is reached. By loading the inert gas with the trioxane and water containing vapor mixtures until close to the dew point the best results are to achieve and the apparatus expenses are minimized.

In the separation process according to our invention the entire water portion is theoretically removable from the steam mixture containing the trioxane, water and formaldehyde by partial condensation in the partial condensing means of the first stage. However, since the degree of water separation and the size of the cooling surfaces in the partial condensing means proceed asymptotically the 100% removal of water would require unlimited cooling surface in the partial condensing means. Thus for economical reasons the removal of water in the condensing means is carried out only such that the residual water portion does not disturb the processing of the trioxane into the final pure product. This is the case when the water content of the trioxane condensed in the condenser of the second stage in the presence of the inert gas residual does not exceed 10% by weight.

The condensation temperature of the trioxane-water azeotrope is about 92° C. and the condensation temperature of a water-trioxane mixture with more than 90% by weight trioxane is from 101° to 104° C. at atmospheric pressure. However, the steam containing inert gas and gaseous trioxane leaving the partial condensing means has a temperature of about 58° to 64° C. This temperature is about 46° to 47° C. lower than the normal condensation temperature of either trioxane-water mixture. Thus without the inert gas stream, the entire trioxane-water steam would condense completely in the partial condenser, the azeotrope barrier would not be overcome and the process would not operate effectively.

BRIEF DESCRIPTION OF THE DRAWING

The method of the present invention is illustrated by the following detailed description which is best understood in reference to the drawing in which:

FIG. 1 shows a first embodiment of the method in which the inert gas stream is fed into the lower part of the evaporator in a discontinuous process.

Figure 1:
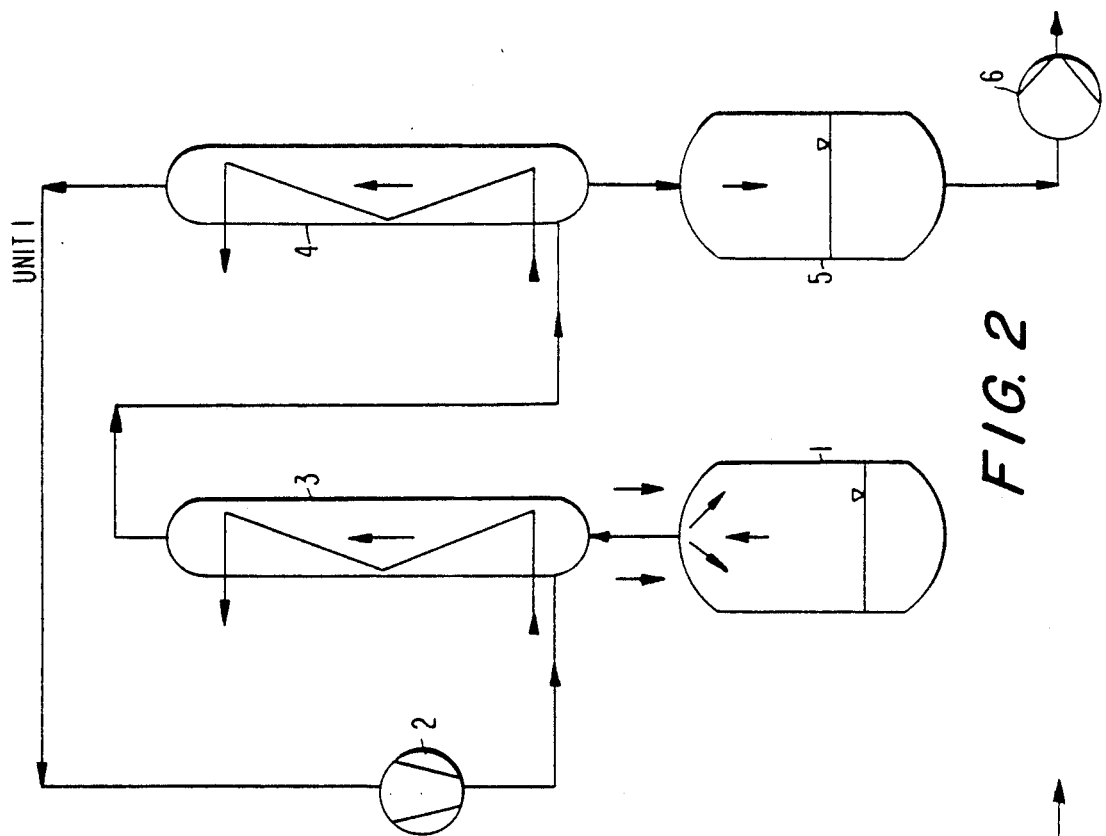
FIGS. 1 to 4 are flow charts of four embodiments of the process for isolating trioxane from aqueous trioxane solutions according to our invention.

The inert gas stream exiting the blower 2 is supplied to the evaporator 1 (distilling vessel) which contains a trioxane-water solution or a trioxane-water-formaldehyde solution at its boiling point at atmospheric pressure. The inert gas-vapor mixture which leaves the evaporator 1 is led through the partial condensing means 3 and cooled there to a temperature of 58° to 64° C. at atmospheric pressure. The condensate obtained in the partial condensing means 3 is returned to the evaporator 1. The inert gas leaving the partial condensing means 3 and actually containing only trioxane and water in a 90 to 10 ratio is supplied for condensation to the condenser 4 wherein the inert gas is separated from the desired product. The trioxane condensate or concentrate produced in the condenser is collected in the separator 5 and fed by pump 6 to other unshown units, advantageously for isolation of pure trioxane without extraction steps at atmospheric pressure.

Figure 2:
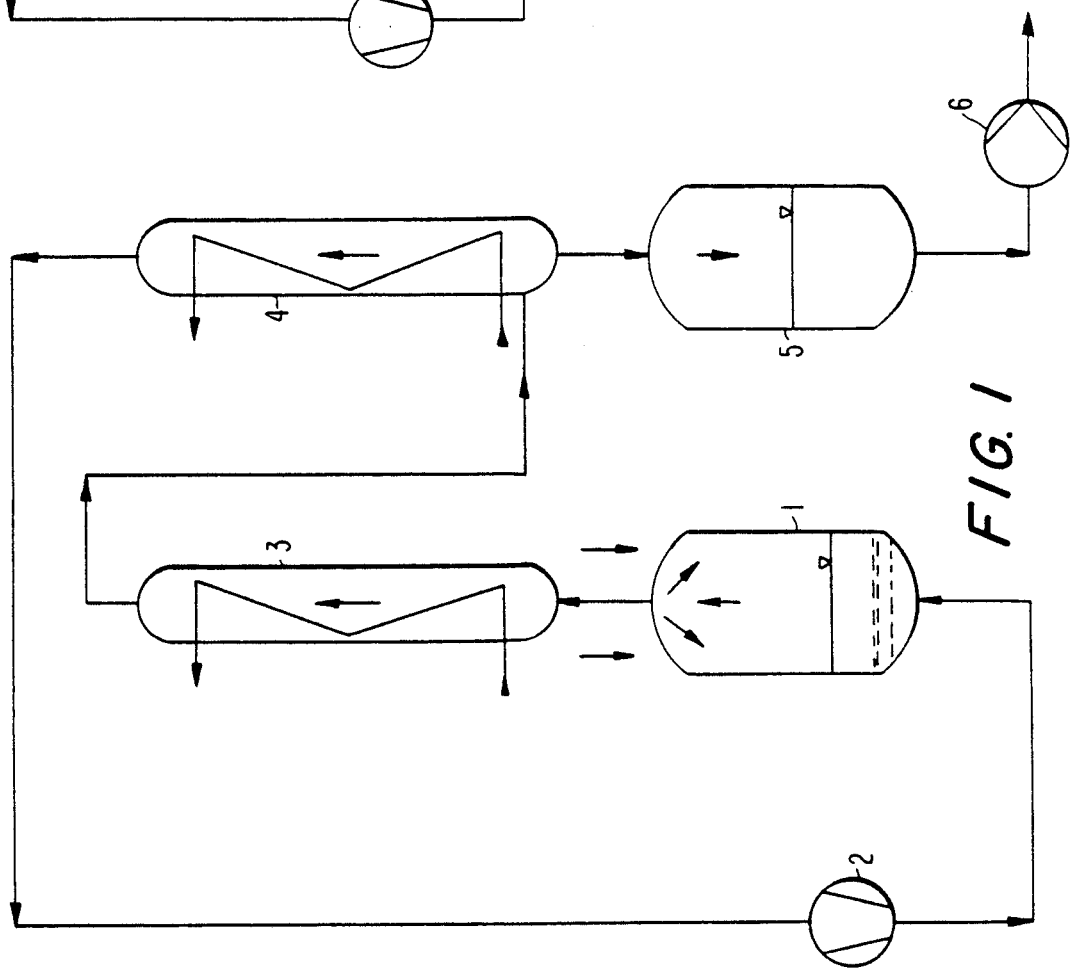

FIG. 2 shows a second embodiment or example of the process according to our invention in which the inert gas stream is introduced into the lower part of the partial condensing means in a discontinuous or batch process.

The same description for the embodiment of FIG. 1 applies to the embodiment of FIG. 2 except that the inert gas stream is supplied to the lower part of the partial condensing means 3 instead of to the evaporator 1.

Figure 3:
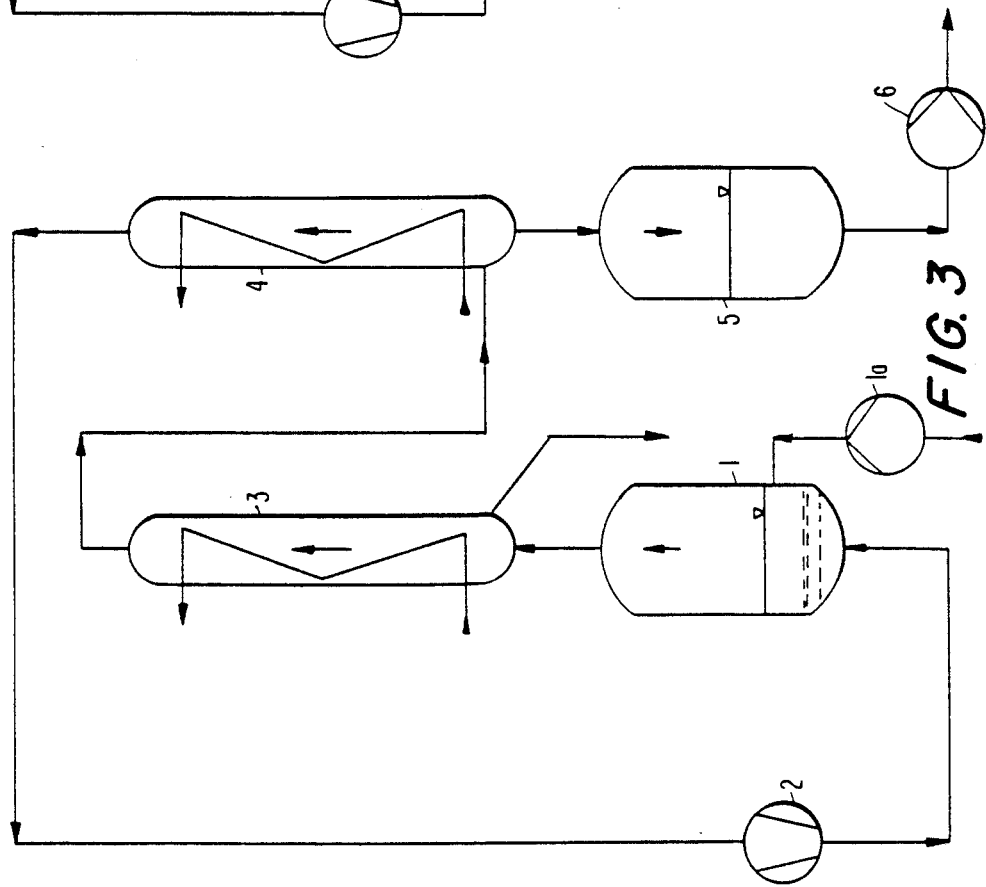

FIG. 3 relates to a third embodiment of the invention, in which the inert gas stream is supplied to the lower part of the evaporator and the aqueous trioxane-containing solution is supplied to the evaporator in a continuous process.

The inert gas stream exiting the blower 2 is led through the evaporator 1 (distilling vessel) which contains a trioxane-water solution, trioxane-water-formaldehyde solution or trioxane-water-formaldehyde acid solution at its boiling point at atmospheric pressure. The liquid level in the evaporator 1 is maintained by supplying the trioxane-water solution or trioxane-water-formaldehyde solution by pump 1a. The inert gas-vapor mixture leaving the evaporator 1 is led through the partial condensing means 3 and cooled there to a temperature of 58° to 64° C. at atmospheric pressure. The condensate obtained in the partial condensing means 3 is withdrawn from the system. The inert gas leaving the partial condensing means 3 and consisting of water and trioxane almost completely in a 10 to 90 ratio is supplied for condensation to the condenser 4, wherein the inert gas is separated from the desired product. The trioxane concentrate produced in the condenser 4 is collected in the separator 5 and supplied by pump 6 to other unshown units, advantageously for isolation of pure trioxane without extraction steps at atmospheric pressure.

Figure 4:
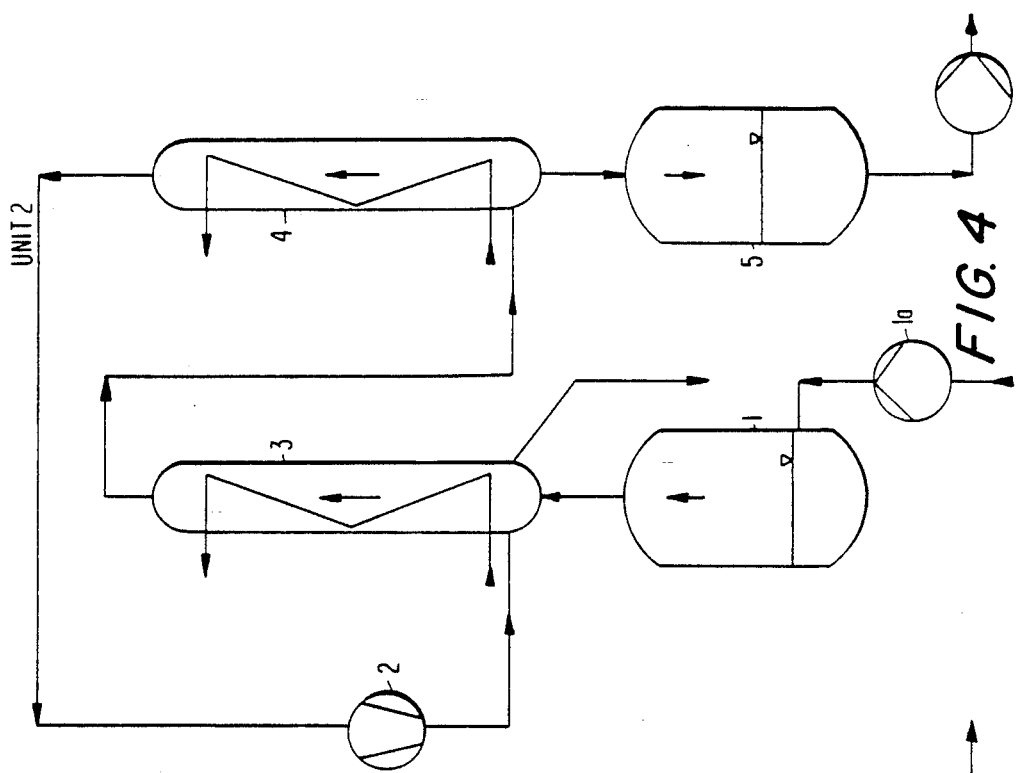

FIG. 4 deals with the fourth embodiment, in which the inert gas stream is supplied to the lower part of the partial condensing means and the aqueous solution containing the trioxane is supplied to the evaporator in a continuous process.

The same description that applies to the embodiment of FIG. 3 applies to the embodiment of FIG. 4 except that the inert gas stream is not supplied to the lower part of the evaporator 1, but instead to the lower part of the partial condensing means 3.

Figure 6:
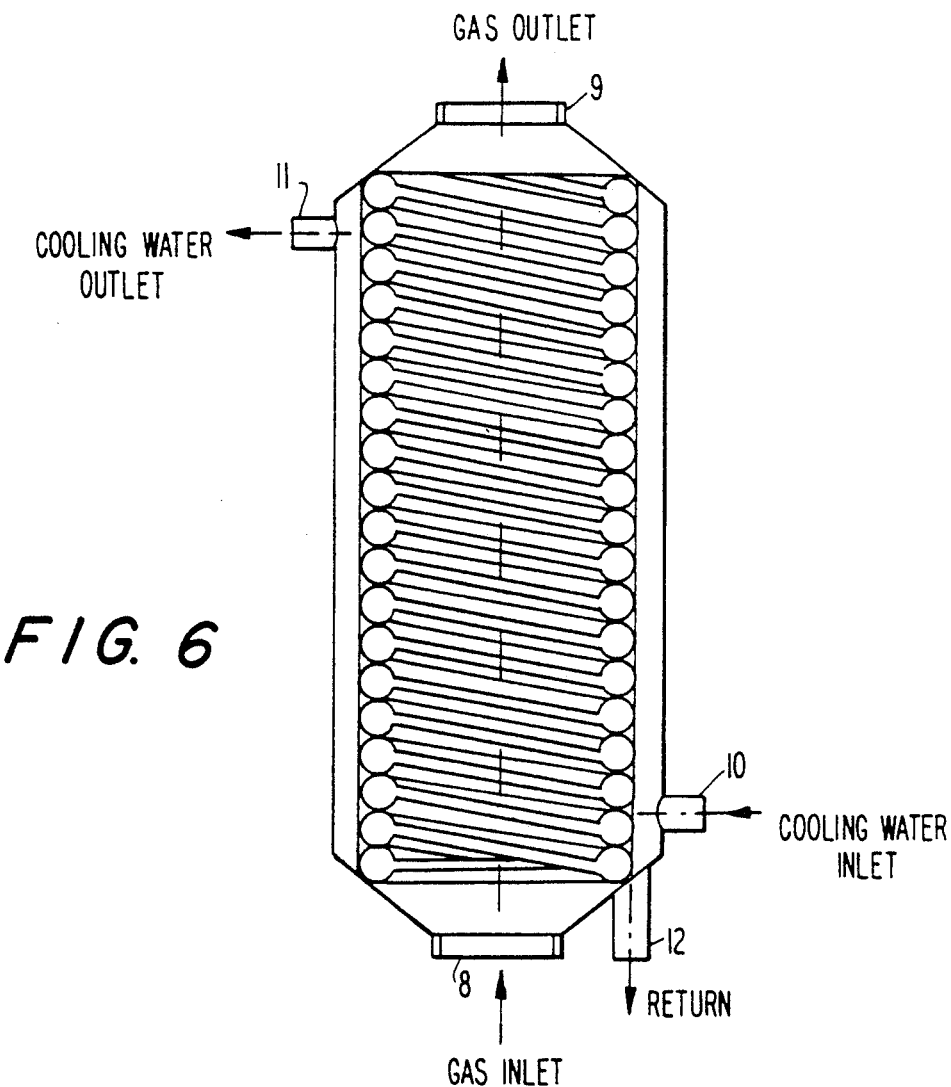
FIG. 6 is a longitudinal cross sectional view of the partial condenser shown in FIG. 5.
Figure 5:
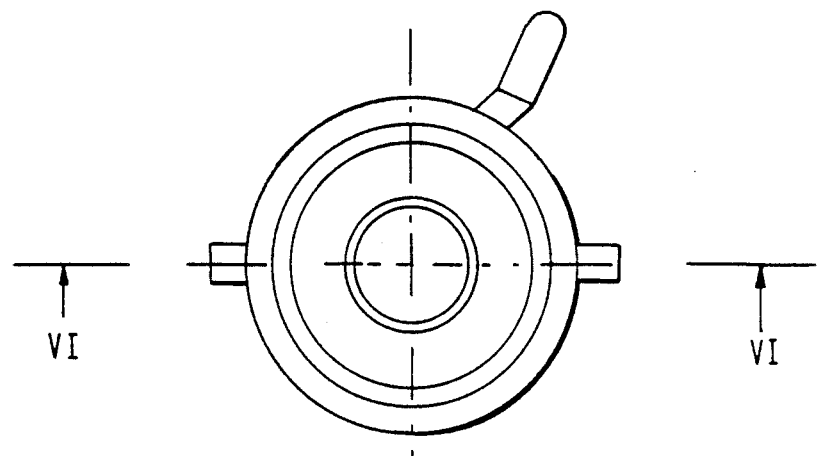
FIG. 5 is a plan view of a partial condenser used in the present methods of isolating trioxane.

FIGS. 5 and 6 are respectively longitudinal cross sectional and top plan views of the partial condenser. The bottom of the partial condenser includes a gas supply valve 8 which permits vapor having a high water content leaving the evaporator to enter, and a gas outlet 9 at the top which permits vapor with a reduced water content to leave. The partial condenser also includes a cooling water inlet 10 near the bottom and a cooling water outlet 11 permitting cooling water to pass through a coil thus effecting partial condensation of the water in the vapor entering through inlet 9. Also found at the bottom of the partial condenser is a return 12 for permitting condensed water to return to the evaporator, if desired.

When an acid-trioxane-formaldehyde solution is the starting material added to the evaporator, a formaldehyde-containing inert gas stream can be used as inert gas supplied from below to the evaporator in the method shown in FIGS. 1 and 3. When as formaldehyde-containing inert gas stream, a formaldehyde gas stream produced by catalytic methanol oxidation is used, the process is continuous in accordance with embodiments of FIG. 3, but is performed with the variation that the inert gas stream is not led directly in circulation.

The most important feature of the invention is the use of the inert gas stream. We have found that because of the presence of the inert gas stream the azeotropic barrier to production of a vapor richer in trioxane than the corresponding azeotropic mixture can be overcome. Thus from the mixture of trioxane, water and in some cases formaldehyde formed in the evaporator, which is then fed to the partial condensing means, practically all of the water and, if present, all available formaldehyde is partially condensed and separated, while the trioxane with the inert gas stream is withdrawn from the partial condensing means and supplied to the condenser in the second stage of the process.

The inert gas stream and the cooling water flow in the partial condensing means in concurrent stream.

The partial condenser is designed so that the condensate immediately after its formation is separated from the inert gas stream.

EXAMPLES

Example I 1,400 grams of aqueous trioxane solution with a trioxane content of 50% by weight is heated in the evaporator while a nitrogen stream is passed therethrough. The nitrogen stream is fed into the lower part of the evaporator and is guided in circulation. The trioxane solution is heated up to boiling, and the steam mixture distilled from the evaporator together with the nitrogen stream is supplied to the partial condenser of the first stage connected directly to the evaporator. The water portion of the steam mixture is partially condensed in the partial condenser at a temperature of from 60° to 62° C. and returned to the evaporator.

The trioxane portion of the mixture freed from water is fed together with the nitrogen stream into the condenser of the second stage of the process which is connected directly to the partial condenser and condensed in the presence of the nitrogen stream. Then it is fed into a collecting vessel or container whereas the nitrogen stream is fed back into the evaporator.

The product contained in the collecting container included 715 g of trioxane with a water content of 0.9% by weight. The yield amounts to 93%. Nitrogen can circulate with the speed of 60 l/h.

The temperature in the evaporator was 92° C., it suddenly raised to 100° C. after the whole trioxane was distilled.

The same results were obtained, if the nitrogen stream leaving the condenser of the second stage was fed back into the lower part of the partial condenser.

Example II

In this example the process of producing trioxane is mainly the same as that in Example I with the difference that the aqueous trioxane solution with a trioxane content of 50% by weight was continuously supplied to the evaporator in the amount of 0.47 l/h, and the water condensed in the partial condenser of the first stage was not fed back to the evaporator, but instead was removed from the system.

The trioxane separated in the condenser of the second stage amounted to 705 g/h; this trioxane had a water content of 8.3% by weight.

Example III

In this example the process of producing trioxane is mainly the same as that of Example I with the difference that instead of the aqueous trioxane solution with a trioxane content of 50% by weight an aqueous trioxane solution with a trioxane content of 70% by weight was heated in the evaporator, that instead of nitrogen carbon dioxide was used as inert gas and that the process was stopped when the trioxane concentrate obtained in the condenser of the second stage contained about 76% by weight trioxane and about 24% by weight water.

The trioxane concentrate was further concentrated by simple distillation to a trioxane with 0.2% by weight water.

Example IV

In this example the process of producing trioxane is mainly the same as that of example I except that instead of the aqueous trioxane solution an aqueous solution containing 42% by weight of trioxane, 43% by weight of water and 15% by weight of formaldehyde was heated up to boiling in the evaporator into which a carbon dioxide stream was fed. The steam mixture distilled from the evaporator together with the carbon dioxide stream was supplied to the partial condenser of the first stage connected directly to the evaporator. The water portion together with the formaldehyde of the steam mixture were partially condensed in said partial condenser at a temperature of from 60° to 62° C. and returned to the evaporator.

The boiling temperature in the evaporator was 89° to 90° C.

The trioxane concentrated in the condenser of the second stage had a water content of 3.9% by weight.

Example V

In this example, instead of the aqueous trioxane solution, 1 l of 64% formalin solution utilized for the production of trioxane and containing 8% by weight of sulfuric acid and 0.8% by weight of phosphoric acid as catalysts, is heated up to boiling in the evaporator into which a nitrogen stream is fed. The distilled steam mixture or synthesis steam which contains water, trioxane and formaldehyde is, together with the nitrogen stream, fed into and passed through the partial condenser of the first stage connected directly to the evaporator. In said partial condenser the gas stream is cooled to a temperature in the range of 60° to 62° C., whereby due to the partial condensation the water portion together with the formaldehyde are condensed and removed from the system.

The resultant trioxane portion of the synthesis steam together with the nitrogen is then fed to the condenser of the second stage connected directly to the partial condenser of the first stage. The steam is condensed in said condenser of the second stage in the presence of the nitrogen stream which is returned to the evaporator. Nitrogen can circulate at a speed of 60 l/h.

The product obtained in this example contains 520 g of trioxane with 9.2% by weight water.

Example VI

The process of producing trioxane in this example is fundamentally the same as in Example V except that gaseous formaldehyde which is introduced into the circulating nitrogen stream is continuously conveyed from the pressure vaporizer to the evaporator at atmospheric pressure.

The amount of trioxane separated from the mixture in the condenser in the presence of nitrogen gas is 832 g/h and its water content is 6.9% by weight.

It will be understood that each of the elements described above, or two or more together, may also find a useful application in other types of methods of isolating trioxane from aqueous trioxane solutions differing from those types mentioned above.

While the invention has been illustrated and described as embodied in a method of isolating trioxane from an aqueous trioxane solution, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A method of isolating trioxane by distillative separation at substantially atmospheric pressure without a solvent extraction step from an aqueous trioxane solution, comprising the steps of heating an aqueous trioxane solution having a trioxane concentration which does not exceed 70% by weight and which does not exceed the concentration of a constant boiling azeotropic mixture obtained from distillation of said aqueous trioxane solution at substantially atmospheric pressure up to boiling in an evaporator to form a trioxane and water vapor-containing steam mixture which leaves the evaporator;

feeding an inert gas stream;

introducing said steam mixture in a first stage together with said inert gas stream through a first stage partial condensing means connected directly to said evaporator, wherein said inert gas stream is fed into said evaporator or said partial condensing means; cooling said steam mixture together with said inert gas stream to a temperature in the range of 58° to 64° C., wherein a water portion of said steam mixture is partially condensed and separated; then in a second stage introducing to a second stage condensing means operating at a temperature of from 30° C. to 50° C. said steam mixture together with said inert gas stream containing a trioxane portion, wherein said trioxane portion is condensed together with a residual water portion and separated from said inert gas stream to form a trioxane concentrate having a trioxane concentration which is greater than that of the corresponding azeotropic mixture such that the azeotropic barrier created by azeotropic formation is overcome, and wherein said method is performed without a solvent extraction step.

2. The method as defined in claim 1, wherein said partial condensation of the first stage is performed in a temperature range between 60° and 62° C.

3. The method as defined in claim 1, wherein said inert gas is fed into a lower portion of said evaporator.

4. The method as defined in claim 1, wherein said inert gas is dispersed in said evaporator with dispersing means.

5. The method as defined in claim 4, wherein said dispersing means include one of filling means, distributing means, sieve means, nozzle means, valve means and bubble cap trays.

6. The method as defined in claim 1, wherein said inert gas is fed either into said evaporator or said partial condensing means in circulation.

7. The method as defined in claim 1, wherein said inert gas is selected from a group consisting of carbon dioxide, nitrogen, noble gas, air and air with an oxygen content of about 10 to 12% by volume.

8. The method as defined in claim 1, further comprising the step of isolating said trioxane from said trioxane concentrate obtained in the second stage by further distillation.

9. The method as defined in claim 1, wherein said aqueous trioxane solution subjected to said distillative separation is a mixture of water and trioxane, which contains about 70% by weight trioxane.

10. The method as defined in claim 1, wherein said aqueous trioxane solution subjected to said distillative separation is a mixture of water, formaldehyde and trioxane which contains about 65 to 60% by weight trioxane, 6 to 16% by weight formaldehyde and 29 to 24% by weight water, and the formaldehyde of said solution is separated together with water portion in the partial condensing means of the first stage.

11. The method as defined in claim 1, wherein said aqueous trioxane solution subjected to said distillative separation contains trioxane, water and a formaldehyde, and the formaldehyde of said solution is separated together with the water portion in the partial condensing means.

12. The method as defined in claim 11, wherein said aqueous trioxane solution contains said trioxane, water and formaldehyde in a ratio of about 35:48:17.

13. The method as defined in claim 11, wherein said aqueous trioxane solution further contains an acid.

14. The method as defined in claim 13, wherein said aqueous trioxane solution contains said formaldehyde in a concentration of 30 to 70% by weight and has a pH which corresponds to that of an aqueous sulfuric acid solution of 0.5 to 25% by weight sulfuric acid.

15. The method as defined in claim 14, wherein said aqueous trioxane solution has a formaldehyde concentration of 50 to 65% by weight.

16. The method as defined in claim 14, wherein said inert gas stream contains formaldehyde and is supplied to the lower portion of said evaporator.

17. The method as defined in claim 14, wherein said inert gas stream contains formaldehyde and said formaldehyde is produced by catalytic methanol oxidation.

18. The method as defined in claim 1, wherein said distillative separation is performed continuously, and the separated water portion of said steam mixture condensed in said partial condensing means is fed back to said evaporator.

19. The method as defined in claim 1, wherein said distillative separation is performed continuously, and the separated water portion of said steam mixture condensed in said partial condensing means is removed.

* * * * *